United States Patent
Darcy et al.

(10) Patent No.: US 11,775,774 B2
(45) Date of Patent: Oct. 3, 2023

(54) OPEN INPUT EMPATHY INTERACTION

(71) Applicant: WOEBOT LABS, INC., San Francisco, CA (US)

(72) Inventors: Alison Darcy, San Francisco, CA (US); Jade Daniels, San Francisco, CA (US); Kim Goodwin, San Francisco, CA (US); Casey Sackett, San Franciso, CA (US)

(73) Assignee: WOEBOT LABS, INC., San Francisco, CA (US)

( * ) Notice: Subject to any disclaimer, the term of this patent is extended or adjusted under 35 U.S.C. 154(b) by 0 days.

(21) Appl. No.: 17/870,975

(22) Filed: Jul. 22, 2022

(65) Prior Publication Data
US 2023/0026871 A1    Jan. 26, 2023

Related U.S. Application Data

(60) Provisional application No. 63/225,153, filed on Jul. 23, 2021.

(51) Int. Cl.
*G06F 40/35* (2020.01)
*G06F 40/289* (2020.01)
(Continued)

(52) U.S. Cl.
CPC ............ *G06F 40/35* (2020.01); *G06F 40/289* (2020.01); *G16H 20/70* (2018.01); *H04L 51/02* (2013.01)

(58) Field of Classification Search
None
See application file for complete search history.

(56) References Cited

U.S. PATENT DOCUMENTS 8,170,609 B2 * 5/2012 Hedtke ................ A61B 5/7275
600/301
2017/0262755 A1 * 9/2017 Takeuchi .............. G06F 40/279
(Continued)

FOREIGN PATENT DOCUMENTS

WO         2019018280 A1      1/2019
WO     WO-2022174161 A1 *    8/2022

OTHER PUBLICATIONS

Extended European Search Report for Application No. EP 22186577.7 dated Dec. 20, 2022; pp. 15.
(Continued)

*Primary Examiner* — Richa Mishra
(74) *Attorney, Agent, or Firm* — NIXON PEABODY LLP

(57) ABSTRACT

A chatbot capable of empathic engagement with a user is disclosed. An identified trend in a user's mood or goals between a first time and a second time can be associated with open input (e.g., open text string input) from the user. As the user's mood or goals continue to be tracked, a subsequent trend can be identified that is the same as, similar to, different from, or opposite to the first identified trend. The user can then be automatically engaged based on the open input associated with the first identified trend. In an example, a user may input thoughts or reasons why they have been having a positively trending mood over a duration of time. The chatbot can then repeat or otherwise use those same thoughts or reasons to engage the user empathically when the chatbot detects that the user is experiencing a negatively trending mood.

27 Claims, 5 Drawing Sheets

(51) Int. Cl.
    H04L 51/02  (2022.01)
    G16H 20/70  (2018.01)

(56) References Cited

U.S. PATENT DOCUMENTS

| | | | |
|---|---|---|---|
| 2019/0370412 A1* | 12/2019 | Hammontree | G06F 40/211 |
| 2020/0020247 A1* | 1/2020 | Simpson | G09B 19/00 |
| 2020/0214626 A1* | 7/2020 | Boyle | A61B 5/6896 |
| 2021/0182496 A1* | 6/2021 | Shi | G06F 40/30 |

OTHER PUBLICATIONS

Alison Darcy, et al.: "Evidence of Human-Level Bonds Established With a Digital Conversational Agent: Cross-sectional, Retrospective Observational Study"; JMIR Formative Research; vol. 5, No. 5, May 11, 2021; XP093006586; pp. 7.

Junjie, Yin, et al.: "A Deep A Learning Based Chatbot for Campus Psychological Therapy", Arxiv. Org, Cornell University Library; Oct. 9, 2019; XP081515836; pp. 31.

Daniel Jurafsky, et al.: "Speech and Language Processing -An Introduction to Natural Language Processing, Computational Linguistics, and Speech Recognition—Third Edition Draft"; Oct. 16, 2019; XP055837804; pp. 31.

Timothy Wallace Bickmore: "Relational Agents: Effecting Change through Human-Computer Relationships" Dec. 15, 2014; XP0551502; pp. 284.

* cited by examiner

OPEN INPUT EMPATHY INTERACTION

CROSS-REFERENCE TO RELATED APPLICATIONS

The present application claims the benefit of U.S. Provisional Patent Application No. 63/225,153 filed Jul. 23, 2021 and entitled "OPEN INPUT EMPATHY INTERACTION," which is hereby incorporated by reference in its entirety.

TECHNICAL FIELD

The present disclosure relates to human-computer interaction generally and more specifically to chatbots and similar tools.

BACKGROUND

Natural language processing (NLP) is used in many fields to provide a comfortable and relatable interface for various purposes. Users can communicate with a computer system via natural language, such as through text input (e.g., typing a message) or audio input (e.g., speaking a message). The computer system then attempts to determine an intended meaning associated with the received input. For example, in the field of human psychology, artificial intelligence systems can use NLP to interact with the user and provide helpful tools, commentary, or other conversation with the user in a natural and comfortable fashion.

NLP techniques very often rely on classifying input text into certain classifications, then using those classifications to generate a response. For example, a user speaking to an automated phone system can say "I'd like to speak to a representative about my order status," and the automated phone system can categorize the input phrase as "order status" and transfer the user to the appropriate department associated with order status. However, limitations in a computer system's ability to interpret and interact with users can make the computer system ineffective for certain types of communications.

In the field of human psychology, empathy is a powerful and important tool to engage a patient and provide effective therapy. In human-human interactions, empathy is a core technique for establishing and maintaining a therapeutic alliance between the therapist and client, which can be important to gain the client's trust and participation in the therapy. However, when a computer system attempts to mimic empathetic communication using current technologies, the interactions fall short and are often interpreted by the user as non-genuine or uncanny, leading to a breakdown of trust and an overall failure of the therapeutic alliance and human-computer relationship, which can be detrimental to the efficacy of the therapy.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, supplemented by this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include a computer-implemented method comprising receiving a first evaluation associated with a goal at a first time and receiving a second evaluation associated with the goal at a second time. The method further includes determining a trend using the first evaluation and the second evaluation. The trend is associated with a period of time between the first time and the second time. The method further includes presenting an explanation request in response to determining the trend. The method further includes receiving an explanation response containing an explanation phrase. The method further includes storing the explanation phrase in association with the trend. The method further includes receiving a third evaluation associated with the goal at a third time. The method further includes determining a subsequent trend using the third evaluation. The subsequent trend is associated with a period of time including the third time. The method further includes presenting an empathic communication in response to determining the subsequent trend. The empathic communication is associated with the goal. Presenting the empathic communication includes accessing a recipe database; selecting a recipe from the recipe database using the subsequent trend; and generating the empathic communication using the selected recipe and the explanation phrase. The empathic communication includes the explanation phrase.

Embodiments of the present disclosure include a system comprising one or more data processors; and a non-transitory computer-readable storage medium containing instructions which, when executed on the one or more data processors, cause the one or more data processors to perform the above method.

Embodiments of the present disclosure include a computer-program product tangibly embodied in a non-transitory machine-readable storage medium, including instructions configured to cause a data processing apparatus to perform the above method.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
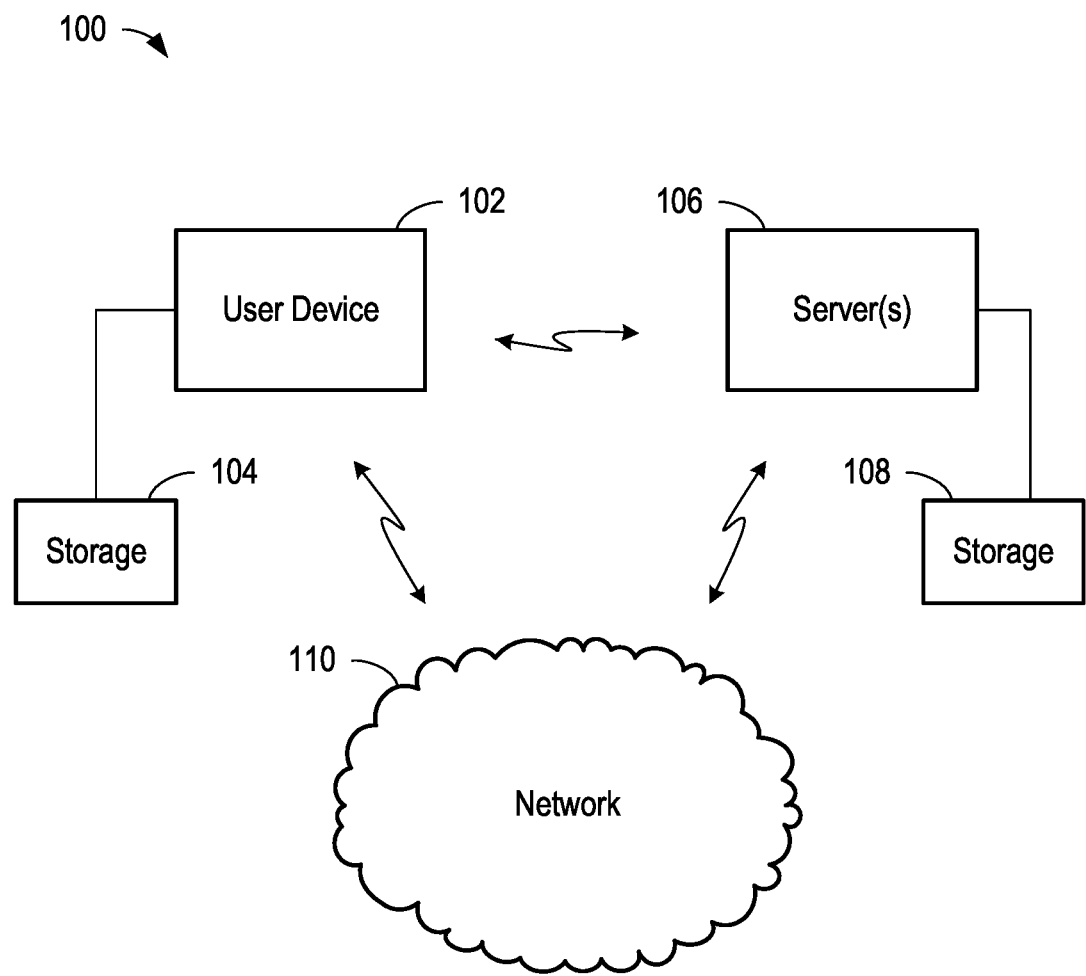
FIG. 1 is a schematic diagram depicting a computing environment according to certain aspects of the present disclosure.

Certain aspects and features of the present disclosure relate to chatbot interactions that empathically engage a user using open inputs (e.g., open text inputs). An identified trend in a user's mood or goals between a first time and a second time can be associated with open input (e.g., open text string input) from the user. As the user's mood or goals continue to be tracked, a subsequent trend can be identified that is the same as, similar to, different from, or opposite to the first identified trend. The user can then be automatically engaged based on the open input associated with the first identified trend. In an example, a user may input thoughts or reasons why they have been having a positively trending mood or goal over a duration of time. The chatbot can then repeat or otherwise use those same thoughts or reasons to engage the user empathically when the chatbot detects that the user is experiencing a negatively trending mood or goal.

Aspects and features of the present disclosure can be used in various environments and for various purposes. In some cases, aspects and features of the present disclosure enable a computer system to engage a user with empathic communications, which can be especially useful in certain human-computer interactions, such as artificial intelligence chat-based tools, commonly known as chatbots. In some cases, the present disclosure can be especially useful when used with chatbots used for therapy, such as the monitoring and/or treatment of mental health disorders. In such cases, not only can it be important and helpful to engage a user with empathetic communications, but it can be especially important to establish and protect the trust that is built up through continued interactions between the user and the chatbot.

In cases where a chatbot is used, inputs are often received in the form of text selected from a list or entered into a field, although that need not always be the case. For example, in some cases, individuals can speak or dictate to the chatbot. As described in further detail herein, empathic communications can be generated through the use of explanation phrases, which can be provided as free text. Free text, also known as open text, can include user-provided input that is not constrained to a selected list of responses, but rather supplied by the user in the user's own phrasing. For example, in response to a prompt asking how are you feeling today, a constrained text response may include a selection between "good," "bad," and "fine," whereas a free text response may include a text string entered into a field by the user using a keyboard (e.g., "I'm feeling excellent today!! !" or a series of emoticons). The free text response can thus include much more useful content than simply the underlying categorization of its text.

While described with reference to a chatbot in many places herein, certain aspects and features of the present disclosure can be used for other purposes, such as to provide empathic responses in other human-computer interactions, such as voice-activated devices (e.g., voice-activated assistants), voice-activated telephonic prompts (e.g., a voice-activated menu service for a telephone line), and the like. Certain aspects and features of the present disclosure can also be used to facilitate empathic communications in human-human interactions, such as text-based or audio-based communications between individuals locally or remotely. For example, a therapist treating a patient may make use of a system that automatically generates empathic communications based on prior goal evaluations to quickly and automatically generate one or more suggested empathic communications without the therapist needing to spend long periods of time reviewing notes to generate their own empathic communication. The therapist can then quickly use the suggested empathic communication directly or put the suggested empathic communication into their own words. Thus, the time between a patient's comment and the therapist's empathic response can be significantly reduced when using certain aspects and features of the present disclosure, which can provide a significant therapeutic benefit to the patient.

Certain aspects and features of the present disclosure are especially useful in providing empathic responses to a user of a chatbot used for therapy. It is well recognized that employing empathy can be extremely helpful and important in providing therapy to patients. In human-human interactions, empathy can be achieved by a treatment professional listening to and understanding the experiences, feelings, or thoughts of the patient, then engaging the patient in a fashion dictated by this understanding. Current chatbot technology does not have the ability to truly understand the experiences, feelings, or thoughts of a user, so other techniques must be used to nevertheless provide empathic communications to a user.

Empathic communications are communications designed to evoke a sense of empathy in the receiver. Empathic communications can include communications that make use of the receiver's own words or phrases, from at a first time, during a future communication at a later time that is related to the first time (e.g., related by subject, sentiment, mood, and the like). In some cases, empathic communications make use of a receiver's own words or phrases by including or incorporating the words or phrases into the communication. In some cases, empathic communications make use of a receiver's own words or phrases by generating a communication that mimics or is similar to the receiver's own words or phrases.

Certain aspects and features of the present disclosure relate to providing empathic communications in association with a goal. The goal can be any suitable achievable state or measurement (e.g., objective measurement or subjective measurement) for which an evaluation can be obtained. Examples of goals include i) mood (e.g., being happy); ii) performing a task a threshold number of times per period of time (e.g., engaging the chatbot at least three times a week); iii) reducing pain; iv) avoiding anger; v) managing a condition (e.g., managing anxiety when stressed); vi) avoiding unwanted thoughts; vii) engaging in relationships; viii) or the like. Evaluations of a goal can be numerical (e.g., on a scale of 1-10), enumerated (e.g., "bad," "poor," "fair," and "good"), or any other technique for generating a comparable evaluation. In some cases, the evaluation can be considered and/or stored as a score (e.g., a numerical score). In some cases, the goal can be mood, in which case evaluation of the goal can result in a score indicative of the user's mood, such as a score of 1-10 where 1 is indicative of a very undesired or unhappy mood and 10 is indicative of a very desired or very happy mood.

Certain aspects and features of the present disclosure involve evaluating a goal at a first and second time, then determining a trend between the first and second times. Once a trend is determined, then the system can request additional information from the user in the form of an explanation response, which can include a free text explanation phrase and any other optional input data. Then, when the goal is evaluated at a later time and a subsequent trend is determined, the explanation phrase can be leveraged by the system to generate and present an empathic communication to the user.

Evaluating a goal can include prompting the user to provide a subjective or objective evaluation of the goal. For example, for a mood, the system can ask the user how they are feeling and provide a constrained set of options from which the user may choose their response (e.g., numbers between 1-10 or a set of enumerated responses).

Once at least two goal evaluations are collected, the goal evaluations can be compared to identify a trend. Any suitable trends can be detected. In an example, a set of possible trends can include i) inclining; ii) declining, or iii) steady (e.g., neither inclining nor declining). In another example, another set of possible trends can include i) inclining rapidly, ii) inclining slowly, iii) steady, iv) declining slowly, v) declining rapidly, or vi) wavering (e.g., repeated periods of inclining and declining). Any other suitable trend can be used.

In some cases, determining a trend can include determining that a trend is the same as, similar to, different from, or opposite to a previous trend. For example, when a move from a goal score of 3 to 6 is detected in a 7 day window, that trend can be compared with a subsequent trend, which can be determined to be the same as (e.g., 3 to 6 or 5 to 8 in a subsequent 7 day window), similar to (e.g., 4 to 5 or 6 to 8 in a subsequent 7 day window), different from (e.g., 3 to 2 or 6 to 4 in a subsequent 7 day window), or opposite to (e.g., 6 to 3 or 5 to 2 in a subsequent 7 day window). In some cases, determining a trend can include determining that a trend is consistent with (e.g., the same as or similar to) or inconsistent with (e.g., different from or opposite to) a previous trend.

In some cases, identifying a trend can include identifying a trend in the goal evaluations and/or other data associated with the goal evaluations. For example, in some cases a trend can be determined based additionally on or entirely on clinical assessments. In another example, in some cases a trend can be determined based additionally on or entirely on open input (e.g., free text).

Once a trend is determined, the system can present an explanation request. The explanation request can be a prompt designed to have the user provide an explanation response. The explanation request can be a prompt asking for an explanation about why the trend is occurring. For example, the explanation request can ask the user what they think contributed to the positive or negative change.

In an example, when the user's mood is improving, the system can prompt the user for information about why the user's mood is improving or what they are feeling or thinking in that moment. The system can allow the user to respond in free text, thus allowing the user to provide the explanation phrase in their own words, using terms and phrases that are meaningful to the user and the user's current experiences, feelings, or thoughts. Then, if the system detects that the user's mood is declining at a future time, the system can leverage the explanation phrase to generate and present an empathic communication that engages the user using terms and phrases that are meaningful to the user and that may help the user understand why their mood is declining, and ultimately help the user improve their mood.

In an example, while the user's mood is improving, the user may provide an explanation phrase of "I have been exercising every other day and have so much more energy because of it!" Then, when the system detects that the user's mood is declining, it may provide an empathic communication, such as "It seems things have been difficult lately. A couple weeks ago, you said that you 'have been exercising every other day and have so much more energy because of it!' Do you think this might help turn things around for you?"

In another example, while the user's mood is improving, the user may provide an explanation phrase in the form of a big smile emoticon and a thumbs up symbol (e.g., "☺👍"). Then, when the system detects that the user's mood is declining, it may provide an empathic communication such as, "It looks like you've had a difficult week. I'd like to see you feeling "☺👍" again. Let's try some exercises . . . ." Use of some or all of the user's own explanation phrase can act as a showing of empathy and can improve user engagement.

As used herein, input provided as free text can be referred to as an input phrase. An input phrase can be provided, such as via text entry in a chat box, by typing text (e.g., on a mechanical or onscreen keyboard), by speaking words aloud, or otherwise. The term input phrase is inclusive of any suitable collection of inputs that conveys linguistic meaning, such as a single word, multiple words, a single sentence, multiple sentences, or even symbols (e.g., emoticons and the like). The input phrase can be pre-processed as necessary to achieve a standard type of input for the classifiers (e.g., an audio signal can be processed through a speech-to-text processor to generate corresponding text). As used herein, the term explanation phrase can be an input phrase, optionally pre-processed (e.g., to remove extraneous words or characters, to correct detected spelling or typing errors, to change tense or subject (e.g., from "I feel great" to "you feel great" or "you felt great"), or the like).

The explanation phrase can be stored in a database, such as in association with one or more goal evaluations and/or a determined trend between goal evaluations. The database can be specific for each user. For example, after using certain aspects and features of the present disclosure for a time, a database for a given user may include a first phrase associated with a positive trend in mood and a second phrase associated with a negative trend in mood. In some cases, when an explanation phrase is received as an explanation response, the explanation phrase can be pre-processed to determine if it is the same as or substantially similar to an existing explanation phrase in the database, in which case the new explanation phrase may not need to be stored.

In some cases, multiple explanation phrases can be used to generate an empathic communication. For example, if a first explanation phrase "A" is associated with an improvement in mood and a second explanation phrase "B" is associated with a decline in mood, an example empathic communication can be "I notice you have been feeling unhappy lately. In the past, you have said A when you were happy and B when you were sad. Let us try to move from B to A." By leveraging the user's own explanation phrases, the empathic communication can carry empathic weight.

In some cases, an explanation phrase can be pre-processed by being passed through a copout classifier. The copout classifier can be any suitable classifier (e.g., a machine learning classifier trained on a dataset of explanation phrases in addition to and/or including known copout phrases) capable of identifying whether a received explanation phrase is or is not a copout. A copout includes a response that is determined to be i) non-responsive to the prompt (e.g., non-responsive to the explanation request), ii) indicative that the user does not wish to respond to the prompt, and/or iii) responsive to the prompt but evasive or conveying low informational weight. For example, in response to the question "You have been happy recently. Is there anything that has been making you especially happy recently?" some example copout phrases include: i) "What time is it?"; ii) "Skip question"; and iii) "Nothing really." Other types of copouts may exist. In some cases, a copout classifier can be further trained based on subsequent feedback from a user indicative that a phrase previously identified as a useful explanation phrase (e.g., not a copout) was in fact not a useful explanation phrase, and thus potentially a copout. In some cases, the copout classifier can be universal, such as a single, trained machine learning classifier used across multiple users. In some cases, however, a general copout classifier can be initially provided, and interactions with the user can be used to further train that general copout classifier for that user, in which case the further trained copout classifier can be stored and later used as an individual copout classifier for that user. In some cases, one or more copout classifiers may be trained for different types of conversations or points in a given conversation. For example, the copout classifier used for a particular point in a conversation can be selected based on how the previous prompt is worded and/or the types of responses expected to be received at that point in a conversation. As used herein, any classifier, including a copout classifier, can be implemented as a machine learning classifier, a regular expression classifier, or a combination of the two.

Empathic communications can be generated using explanation phrases using various techniques. In some cases, an empathy response recipe can operate as a template to which explanation phrases can be insert. For example, the empathy response recipe can provide a phrase containing a field that is replaced with the explanation phrase. In some cases, the empathy response recipe can be an algorithm or set of instructions for how the empathic communication is generated from the explanation phrase. For example, different information extraction techniques (e.g., named entity recognition) can be used to identify nouns and verbs from the explanation phrases, and/or sentiment analysis can be performed on the explanation phrase to obtain sentiment information. Other NLP techniques can be used to obtain information about the explanation phrase (e.g., metadata associated with the explanation phrase). In some cases, such metadata can be extracted (e.g., soon after the explanation phrase is supplied, such as in response to receiving the explanation phrase) and stored along with and/or instead of the explanation phrase (e.g., during storing of the explanation phrase). In some cases, however, such metadata can instead be extracted on-the-fly during generation of the empathic communication. The algorithm of the empathy response recipe can cause the empathic communication to be generated using the extracted metadata (e.g., named entities, sentiments, etc.). In an example, a trained machine learning algorithm can be used to generate the empathic communication using the information extracted from the explanation phrase. In some cases, different empathy response recipes can dictate different combinations of metadata to be used and/or different techniques (e.g., different trained algorithms, different templates, or the like) for generating the empathic communication using the selected metadata.

Aspects and features of the present disclosure provide various improvements to the technological process of natural language processing and human-computer interaction, especially with respect to chatbots, such as therapy chatbots. Examples of such improvements include an ability to engage a user with empathic communications in a fashion that comes across as natural and genuine. Further improvements include generation of a user-specific database of explanation phrases in association with goal trends, which can be leveraged to generate empathic communications. Further improvements include the ability to quickly generate empathic communications and provide the empathic communications within a short time window to optimize efficacy of the empathic communication.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic diagram depicting a computing environment 100 according to certain aspects of the present disclosure. The environment 100 can be located in a single physical location or can be distributed about multiple physical locations. Environment 100 can be used to implement an NLP system, such as being used to receive input phrases, identify trends, request and receive explanation phrases, and use explanation phrases to generate empathic communications, such as described in further detail herein. Environment 100 is an example of a suitable environment for implementing the NLP system, although other environments can be used instead.

Environment 100 can include one or more user devices 102 and/or one or more servers 106. For example, some environments contain only a single user device 102, and some environments contain a user device 102 and one or more server(s) 106. In some cases, multiple user devices 102 can be used. In some cases, other devices can be used. When multiple devices are used, each device can be communicatively coupled together, such as via a direct connection (e.g., a wired connection, such as a universal serial bus (USB) connection, or a wireless connection, such as a Bluetooth connection) or via network 110 (e.g., via a network interface). Network 110 can be any suitable network, such as a local area network, a wide area network, a cloud, or the Internet.

An individual can interact with the NLP system to establish one or more goals, provide evaluations related to each goal, provide explanation phrases associated with identified trends, and otherwise interact with the NLP system. The NLP system can present various communications to the user (e.g., via text or audio), such as an empathic communication, as disclosed herein. In some cases, the NLP system includes a chatbot, although other techniques for interacting with the user can be used.

The NLP system can include software executable on one or more of the devices of the environment 100 and usable to interact with a user and otherwise perform certain aspects and features of the present disclosure. The NLP system can be implemented on a single device (e.g., on user device 102) or can be implemented across multiple devices (e.g., any combination of one or more user devices 102 and sever(s) 106). In an example case, the NLP system is implemented entirely on the user device 102. In another example case, the NLP system can include an interface operating on the user device 102 and a backend operating on the server(s) 106. In such an example, the backend can perform the various functions disclosed herein, such as receiving evaluations, determining trends, presenting explanation requests, receiving explanation responses, storing explanation phrases, and generating and presenting empathic communications.

A user device 102 can act as a primary mode of interaction for one or more individuals to interact with (e.g., provide inputs to and receive prompts from) the NLP system. Examples of user devices 102 include any suitable computing device, such as a personal computer, a smartphone, a tablet computer, a smartwatch, a smart speaker, or the like.

User device 102 can be operatively coupled to storage 104 to store data associated with applications and processes running on the user device 102. For example, storage 104 can store a database of explanation phrases in association with identified trends; a trained machine learning algorithm used to classify explanation phrases; a recipe database containing recipes for constructing empathic communications; and the like. User device 102 can include any combination of input/output (I/O) devices that may be suitable for interacting with the NLP system, such as a keyboard, a mouse, a display, a touchscreen, a microphone, a speaker, an inertial measurement unit (IMU), a haptic feedback device, or other such devices.

In some cases, user device 102 can include a communication device designed to bridge the NLP system with a separate communication system, such as a telephone system. In some cases, such a communication device can be used to provide input phrases to the NLP system (e.g., via a user establishing an audio connection through a telephone system).

One or more servers 106 can be used to process inputs received from the user, such as inputs received from the user device 102 via the network 110, and take further action (e.g., determine trends, present explanation requests, or generate and present empathic communications). In some cases, the server(s) 106 can perform traditional NLP functions, such as parsing input phrases, converting speech to text, classifying input phrases (e.g., classifying a provided input phrases as a copout phrase or not a copout phrase), and the like. In some cases, however, some or all of such NLP functions can be performed on the user device 102.

In some cases, the server(s) 106 can be operatively coupled to storage 108 to store data associated with applications and processes running on the server(s) 106. For example, storage 108 can store a database of explanation phrases in association with identified trends for each user; global and/or user-specific trained machine learning algorithms used to classify explanation phrases; a recipe database containing recipes for constructing empathic communications; and the like.

As used herein, presenting information (e.g., presenting a prompt or presenting a communication) can include transmitting the information to a user device 102 for presentation and/or presenting the information using the user device 102 and/or the server(s) 106. For example, the server(s) 106 can effect presentation of a communication by i) transmitting the communication to the user device 102 for subsequent presentation to the user; ii) displaying the communication on a screen or other output device coupled to the server(s) 106; and/or iii) generating audio output representative of the communication using a speaker or other output device coupled to the server(s) 106.

Figure 2:
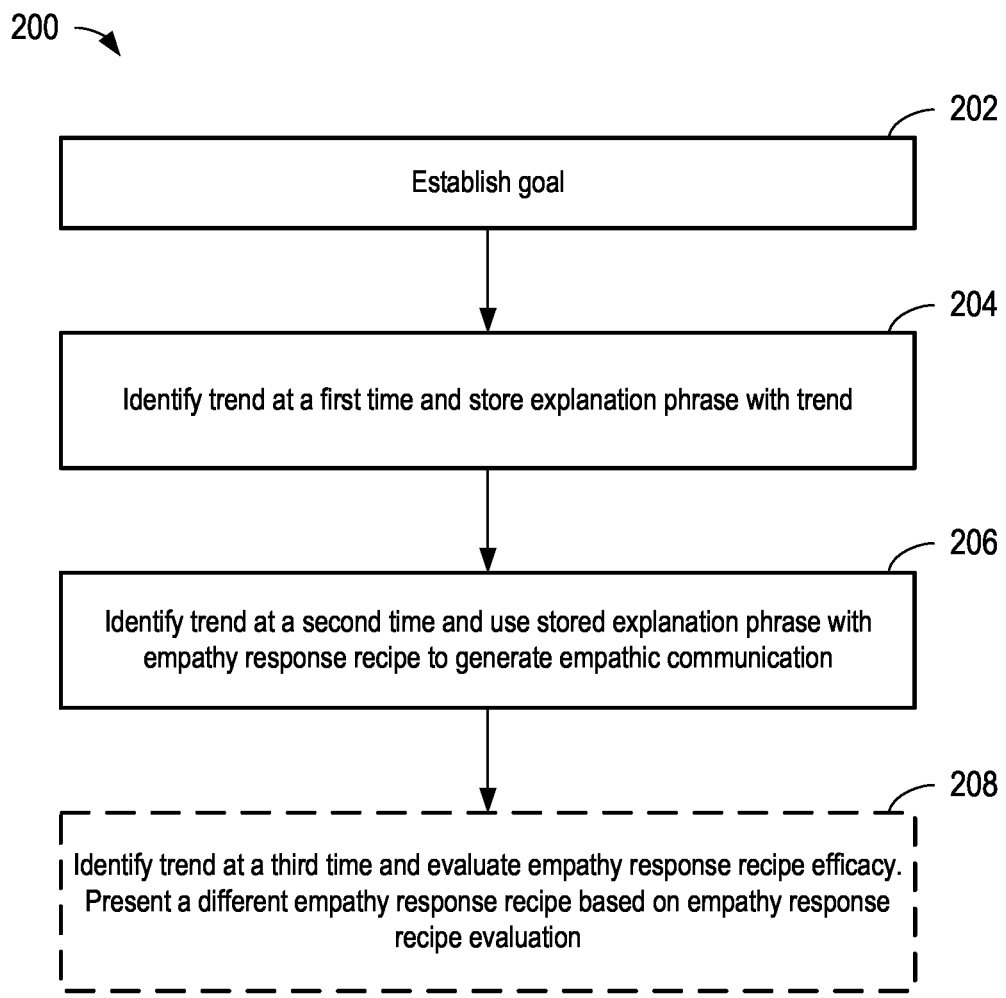
FIG. 2 is a flowchart depicting a process for evaluating a goal and presenting empathic communications according to certain aspects of the present disclosure.

FIG. 2 is a flowchart depicting a process 200 for evaluating a goal and presenting empathic communications according to certain aspects of the present disclosure. Process 200 can be performed using an NLP system, such as the NLP system described with reference to environment 100 of FIG. 1.

At block 202, a goal can be established. Establishing a goal can include optionally presenting a prompt to a user to start a process of establishing one or more goals. In some cases, establishing a goal can include presenting a prompt to the user containing a constrained list of possible goals and/or an open input option to establish a user-defined goal. As an example, when first using the NLP system, the user may be prompted to establish a goal they want to start tracking. In response, the user may select a checkbox near and/or type in "mood" to indicate that they want to track (and improve) their mood.

After a goal is established at block 202, the goal can be periodically evaluated. Evaluation can be user-initiated (e.g., the user can press a button to start a goal evaluation process) or system-prompted (e.g., the system can present a reminder to the user to start the goal evaluation process or can automatically start a goal evaluation process). During a goal evaluation process, the user can provide inputs to the system that are indicative of a progress associated with the goal. For example, when the goal is a mood, the inputs provided during a goal evaluation process can include numerical identifiers or enumerated text identifiers of the user's mood from a poor mood to a great mood.

At block 204, a trend is identified at a first time. Identifying (e.g., determining) the trend at a first time can include comparing a first evaluation to a second evaluation to identify a trend, although any number of evaluations can be used. In some cases, the second evaluation is obtained at least a threshold amount of time after the first evaluation (e.g., at least a day, three days, a week, tens of days, etc.). In some cases, at least a threshold number of evaluations are used to identify the trend. For example, determining a trend can include using the last x number of evaluations to identify the trend.

Once a trend is identified, an explanation request can be presented to the user to prompt the user to provide an explanation response. The explanation request can indicate the type of information desired for the explanation response (e.g., "what were you thinking when you felt this way?" or "How do you feel about this trend?" or "What helped you achieve this trend?"). The explanation response can include an explanation phrase and optionally additional information. The explanation phrase can be open input received from the user. The open input can include text or other characters written by the user in the user's own style. Once the explanation response is received, the explanation phrase can be stored in association with the identified trend. For example, a database entry can include entries such as: "Trend: increasing mood; Phrase: 'I was exercising every day.'"

At block 206, a trend can be identified at a second time. The trend identified at the second time can be the same as the trend identified at block 204 or a different trend. The trend identified at the second time can be based on at least a recent evaluation. For example, the trend identified at this second time can be a trend using the last x number of evaluations up until this recent evaluation, which may or may not include any of the evaluations used to identify the trend at the first time at block 204.

Once the trend is identified at block 206, it can optionally be compared with the trend identified at block 204. Depending on the comparison, on the type of trend identified at block 204, and/or the type of trend identified at block 206, an empathy response recipe can be selected and a stored explanation phrase can be accessed (e.g., the stored explanation phrase associated with the trend from block 204). The empathy response recipe can be selected from a set of empathy response recipes, each of which provides rules or instructions for generating an empathy response using a stored explanation phrase. For example, where A represents the stored explanation phrase, a first recipe may be "In the past, you mentioned that A was helpful to improve your goal," and a second recipe may be "Remember when you spoke about A? You had said it was helpful before." After a recipe is selected, an empathic communication can be generated by applying the stored explanation phrase with the selected empathy response recipe. This empathic communication can then be presented to the user.

In some cases, at optional block 208, a trend can be identified at a third time. The trend identified at the third time can be the same as or different from the trends identified at blocks 204, 206. The trend at the third time can be compared with the trend(s) at the first and/or second times to evaluate the empathy response recipe used at block 206. If it is determined that the trend at the third time is showing an improvement when compared to the trend at the second time, optionally among other determined factors (e.g., such as previous successful use of the empathy response recipe with this user and/or other users), the empathy response recipe used at block 206 may be considered effective. However, if the trend at the third time is showing a decline when compared to the trend at the second time, optionally among other determined factors (e.g., such as previous unsuccessful use of the empathy response recipe with this user and/or other users), the empathy response recipe used at block 206 may be considered ineffective or less-than-optimally effective. The empathy response recipe evaluation can be used to train a model or otherwise generate an indication regarding which empathy response recipes are more or less effective globally and/or for a given user.

While described as identifying a trend at a third time with reference to block 208, any number of subsequent trends can be identified at any subsequent times (e.g., a fourth time, a fifth time, etc.) to further improve performance in the fashion described with reference to block 208.

In some cases, if the empathy response recipe evaluation is indicative that the empathy response recipe used at block 206 was ineffective or less-than-optimally effective, a subsequent empathic communication can be generated using the stored explanation phrase from block 204 and a different empathy response recipe.

Process 200 is described with reference to a single goal, however any number of goals can be used. In some cases, determining trends can include determining trends across multiple goals (e.g., multiple dimensional trends). For example, a first trend may be associated with mood increasing while productivity decreases, a second trend may be associated with mood increasing while productivity increases, a third trend may be associated with mood decreasing while productivity decreases, and a fourth trend may be associated with mood decreasing while productivity increases. Any combination of goals and trend types can be used.

Process 200 is depicted with a certain arrangement of blocks, however in other cases, process 200 can include additional blocks and/or some blocks removed.

Figure 3:
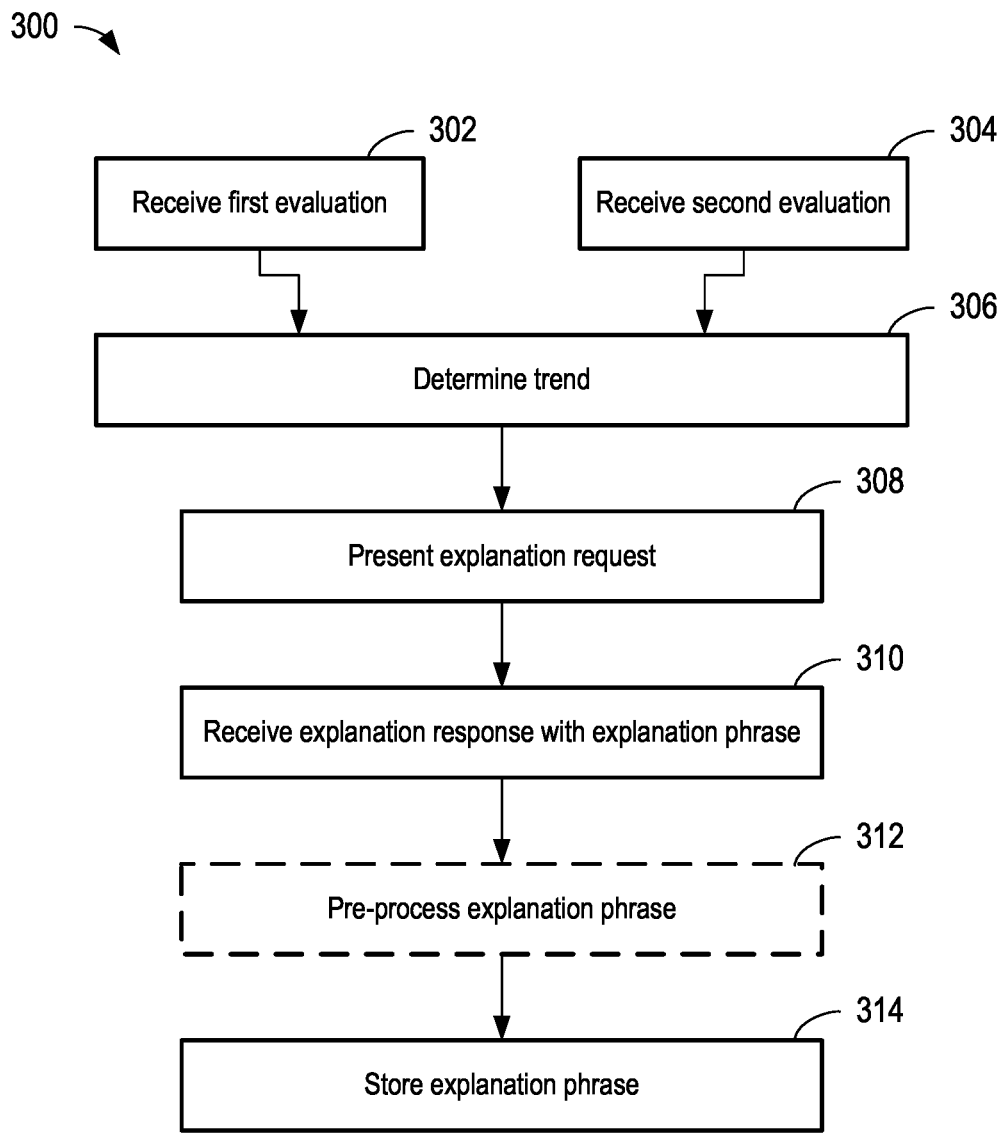
FIG. 3 is a flowchart depicting a process for evaluating a goal and storing an evaluation phrase according to certain aspects of the present disclosure.

FIG. 3 is a flowchart depicting a process 300 for evaluating a goal and storing an evaluation phrase according to certain aspects of the present disclosure. Process 300 can be performed using an NLP system, such as the NLP system described with reference to environment 100 of FIG. 1. In some cases, process 300 can be performed each time a trend is identified in process 200 of FIG. 2, such as at block 204.

At block 302, a first evaluation is received. Receiving the first evaluation can include receiving input from the user indicative of the progress towards a goal. In some cases, receiving the first evaluation at block 302 can include using NLP techniques to associate the received input with a score. The first evaluation is received at a first time.

At block 304, a second evaluation is received. Receiving the second evaluation can include receiving input from the user indicative of the progress towards a goal. In some cases, receiving the second evaluation at block 304 can include using NLP techniques to associate the received input with a score. The second evaluation is received at a second time subsequent to the first time. In some cases, the second evaluation is the immediately subsequent to the first evaluation, although that need not always be the case. In some cases, the second time is at least a threshold amount of time after the first time (e.g., at least 24 hours, three days, or a week after the first time).

At block 306, a trend can be determined using the first evaluation and the second evaluation. Determining the trend at block 306 can include comparing the scores from the first evaluation and the second evaluation, and optionally any additional evaluations between the first evaluation and the second evaluation, to identify a trend. Any suitable technique can be used to identify the trend, such as regression analysis (e.g., linear regression). In some cases, identifying a trend can include identifying a category of trend. In an example, identifying a category of a trend can include identifying the trend as i) increasing; ii) decreasing; or iii) steady. In another example, identifying a category of a trend can include identifying the trend as i) inclining rapidly, ii) inclining slowly, iii) steady, iv) declining slowly, v) declining rapidly, or vi) wavering (e.g., repeated periods of inclining and declining). Any other suitable set of trend categories can be used. In some cases, the use of trend categories can allow trends to be compared with one another easily. In some cases, certain categories may be considered consistent with or inconsistent with other categories. For example, inclining rapidly and inclining slowly might be considered to be consistent with one another, while also each being considered inconsistent with declining slowly and declining rapidly. Other comparison techniques can be used.

At block 308, an explanation request is presented to the user. Presenting the explanation request can include displaying or otherwise presenting a prompt requesting that the user provide an explanation response. In some cases, the explanation request can be designed to urge the user to provide an explanation response in a certain format. For example, an explanation request can be structured to urge the user to provide an explanation response in the form of "I+verb+adjective" or "I was feeling+adjective." In some cases, the explanation request can be designed to urge the user to provide an explanation or other information associated with the thoughts, feelings, or experiences of the user during the time period of the trend determined at block 306 (e.g., the time period between the first evaluation and the second evaluation).

In response to the explanation request, the user can provide the explanation response, which is received at block 310. The explanation response can include an explanation phrase, as well as additional related data (e.g., metadata or other inputs). The explanation phrase is a phrase provided in the user's own style (e.g., in the user's own words or in the user's voice). The explanation phrase can be any suitable phrase (e.g., one or more characters, one or more words, one or more sentences, one or more symbols, etc.). In some cases, such as when the user uses a user device to interact with a chatbot running on a remote server, receiving the explanation response can include receiving the explanation response via a network interface.

At optional block 312, the explanation phrase can be pre-processed. Pre-processing the explanation phrase can include performing any suitable processing on the explanation phrase. In some cases, pre-processing can normalize a format of the explanation phrase. In some cases, pre-processing occurs before the explanation phrase is stored at block 314, although that need not always be the case. In some cases, some or all pre-processing can occur after the explanation phrase is received from storage and before it is used to generate an empathic communication.

In some cases, pre-processing at block 312 includes removing extraneous words or characters (e.g., unnecessary words or characters, or duplicate words or characters). In some cases, pre-processing includes correcting detected spelling or grammatical errors (e.g., "their" instead of "there") or typing errors (e.g., due to use of an onscreen keyboard, such as "hello" instead of "hwllp"). In some cases, pre-processing includes altering the structure of the explanation phrase, such as by changing verb tense, changing the subject, or truncating the phrase.

In some cases, pre-processing at block 312 can include classifying the explanation phrase. Any suitable classifier can be used to generate classification information about the explanation phrase. In some cases, classifying the explanation phrase can include classifying the explanation phrase as a copout or not a copout via a copout classifier. The copout classifier can be used to determine whether or not the received explanation phrase is intended by the user to be a genuine explanation response. A genuine explanation response would be classified as not a copout, and would continue to block 314. However, a non-genuine or non-helpful explanation response would be classified as a copout and may be ignored, although that need not always be the case. As an example, in response to a question about what experiences a user has been undergoing during a time period associated with a trend, the user may supply a blank explanation phrase or a non-genuine explanation phrase (e.g., "exit," "alksdjfals," or "I don't really know"). In such an example, a response of "I don't really know" may be a genuine response from the user, but may nevertheless be classified as a copout if the copout classifier is trained to deem it a non-helpful explanation response (e.g., a response containing a low informational weight for the purpose of reuse in an empathic communication). In some cases, however, a copout classifier can be trained to deem a response such as "I don't really know" as helpful, and therefore not a copout, such as if a suitable empathy response recipe exists to reuse such an explanation phrase (e.g., "The last time you experienced this trend, you told me that 'you don't really know' why you felt that way . . . "). In some cases, a copout includes a response that is determined to be i) non-responsive to the prompt (e.g., non-responsive to the explanation request), ii) indicative that the user does not wish to respond to the prompt, and/or ii) responsive to the prompt but evasive or conveying low informational weight.

At block 314, the explanation phrase can be stored. Storing the explanation phrase can include storing the (optionally pre-processed) explanation phrase in a local or remote storage, such as in a local or remote database. In some cases, storing the explanation phrase at block 314 can include causing a remote device (e.g., a user device or a server) to store the explanation phrase in a storage of the remote device. The explanation phrase can be stored in association with the determined trend from block 306 (e.g., in association with the category of the trend determined at block 306). In some cases, storing the explanation phrase at block 314 can include storing classification information from block 312. For example, a classifier at block 312 can classify a response as a list of adjectives or as a full sentence, which can be stored as classification information in association with the stored explanation phrase. Such classification information can be subsequently accessed and used, such as in the selection of an empathy response recipe.

Process 300 is depicted with a certain arrangement of blocks, however in other cases, these blocks can be performed in different orders, with additional blocks, and/or some blocks removed. For example, in some cases, block 312 is removed. In some cases, block 308 is skipped, and receiving the explanation response at block 308 can be performed automatically in association with receiving the second evaluation at block 304 (e.g., an explanation phrase can be provided by the user when providing the second evaluation at block 304).

In an alternate example case, process 300 can occur without blocks 302, 304, 306, 308; block 310 can be altered such that user input (e.g., an explanation response or other user input) is received and includes an input phrase (e.g., an explanation phrase or other input phrase); and blocks 312, 314 involve pre-processing and storing, respectively, the input phrase.

Figure 4:
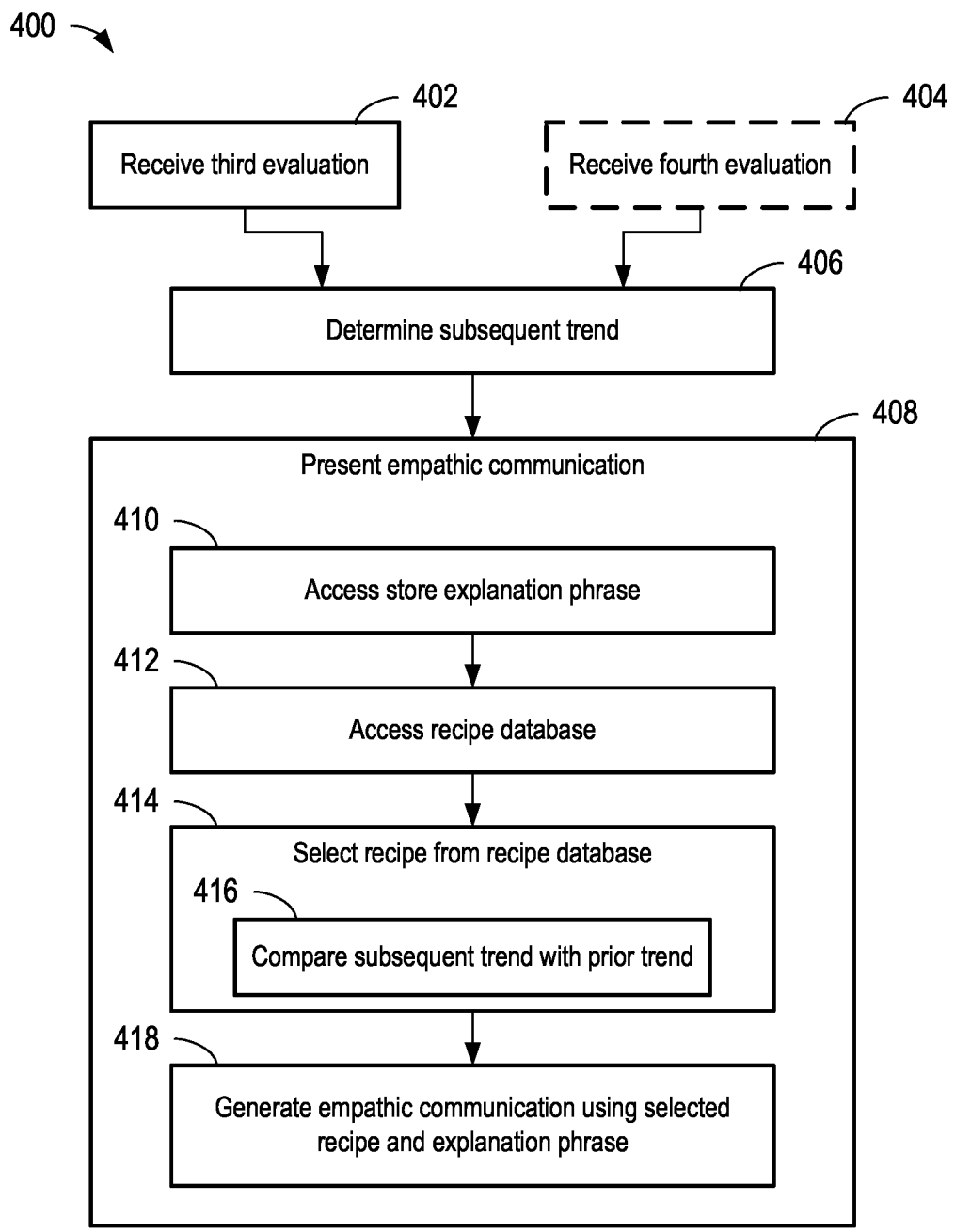
FIG. 4 is a flowchart depicting a process for evaluating a goal and applying a stored evaluation phrase to present an empathic communication according to certain aspects of the present disclosure.

FIG. 4 is a flowchart depicting a process 400 for evaluating a goal and applying a stored evaluation phrase to present an empathic communication according to certain aspects of the present disclosure. Process 400 can be performed using an NLP system, such as the NLP system described with reference to environment 100 of FIG. 1. Process 400 can be performed after an explanation phrase has been stored (e.g., after an occurrence of process 300 of FIG. 3), such as at subsequent times a trend is determined, such as at block 206 of process 200 of FIG. 2.

At block 402, a third evaluation is received. Receiving the third evaluation can include receiving input from the user indicative of the progress towards a goal. In some cases, receiving the third evaluation at block 402 can include using NLP techniques to associate the received input with a score. The third evaluation is received at a third time subsequent to the first time (e.g., first time associated with block 302 of FIG. 3) and second time (e.g., second time associated with block 304 of FIG. 3). In some cases, the third evaluation is the immediately subsequent to the second evaluation, although that need not always be the case. In some cases, the third time is at least a threshold amount of time after the second time (e.g., at least 24 hours, three days, or a week after the first time).

At optional block 404, a fourth evaluation is received. Receiving the fourth evaluation can include receiving input from the user indicative of the progress towards a goal. In some cases, receiving the fourth evaluation at block 404 can include using NLP techniques to associate the received input with a score. The fourth evaluation is received at a fourth time subsequent to the third time. In some cases, the fourth evaluation is the immediately subsequent to the third evaluation, although that need not always be the case. In some cases, the fourth time is at least a threshold amount of time after the third time (e.g., at least 24 hours, three days, or a week after the first time).

At block 406, a trend can be determined using the third evaluation from block 402. In some cases, determining the trend at block 406 can include comparing the scores from the second evaluation and the third evaluation, and optionally any additional evaluations between the second evaluation and the third evaluation, to identify a trend. When a fourth evaluation is received at block 404, determining the trend at block 406 can include comparing the scores from the third evaluation and the fourth evaluation, and optionally any additional evaluations between the third evaluation and the fourth evaluation, to identify a trend. Any suitable technique can be used to identify the trend, such as described with reference to block 306 of FIG. 3.

At block 408, an empathic communication can be presented. Presenting the empathic communication can include transmitting, displaying, or otherwise presenting or causing to be presented the empathic communication. In some cases, presenting the empathic communication includes transmitting the empathic communication to a user device to be displayed on the user device.

Presenting the empathic communication at block 408 can include accessing the stored explanation phrase at block 410. In some cases, accessing the stored explanation phrase can include simply accessing the explanation phrase associated with the immediately previous trend. In some cases, accessing the stored explanation phrase can include uses the subsequent trend determined at block 406 to identify a stored explanation phrase to be used. Identifying the stored explanation phrase to use can include accessing an explanation phrase that is associated with a trend that is the same as, different from, consistent with, inconsistent with, or otherwise related to the subsequent trend from block 406. For example, when a subsequent trend is determined at block 406 to be a negative trend, the stored explanation phrase accessed at block 410 can be that associated with a positive trend.

At block 412, a recipe database can be accessed. The recipe database can be accessed locally or remotely. The recipe database can include a collection of possible recipes for generating empathy communications. At block 414, a recipe to be used can be selected form the recipe database. In some cases, selecting a recipe from the recipe database can be based on the category of trend determined at block 406 and/or the category of trend associated with the stored explanation phrase from block 410. In some cases, selecting a recipe from the recipe database can include comparing the subsequent trend with a prior trend (e.g., the trend associated with the stored explanation phrase from block 410) at block 416. Depending on the comparison, one of a number of recipes can be selected for use. For example, if the subsequent trend is inconsistent with the prior trend, a particular recipe can be selected. As another example, if the subsequent trend is inconsistent with the prior trend and the subsequent trend is a negative trend, a particular recipe can be used.

After a recipe is selected, the empathic communication can be generated at block 418. Generating the empathic communication can include using the selected recipe from block 414 and the explanation phrase from block 410. Generating the empathic communication can include applying the explanation phrase to the selected recipe. In some cases, generating the empathic communication at block 418 and/or accessing the stored explanation phrase at block 410 can include pre-processing the explanation phrase, such as similar to block 312 of FIG. 3. After the empathic communication is generated at block 418, the empathic communication can be presented to the user (e.g., transmitted to the user's user device).

While described with reference to a single explanation phrase, in some cases presenting the empathic communication at block 408 can include accessing two or more explanation phrases and generating the empathic communication using a selected recipe and the two or more explanation phrases.

Process 400 is depicted with a certain arrangement of blocks, however in other cases, these blocks can be performed in different orders, with additional blocks, and/or some blocks removed. For example, in some cases, a default recipe is always used, in which case blocks 412, 414, 416 may be removed and the empathic communication can be generated at block 418 using the default recipe.

In an alternate example case, process 400 can occur without blocks 402, 404, 412, 414, 416; block 406 can include determining any trigger (e.g., identifying a subsequent trend or any other trigger event); and blocks 410 and 418 can include accessing a stored input phrase and generating the empathic communication using at least a portion of the input phrase (e.g., the empathic communication contains at least a portion of the input phrase).

Figure 5:
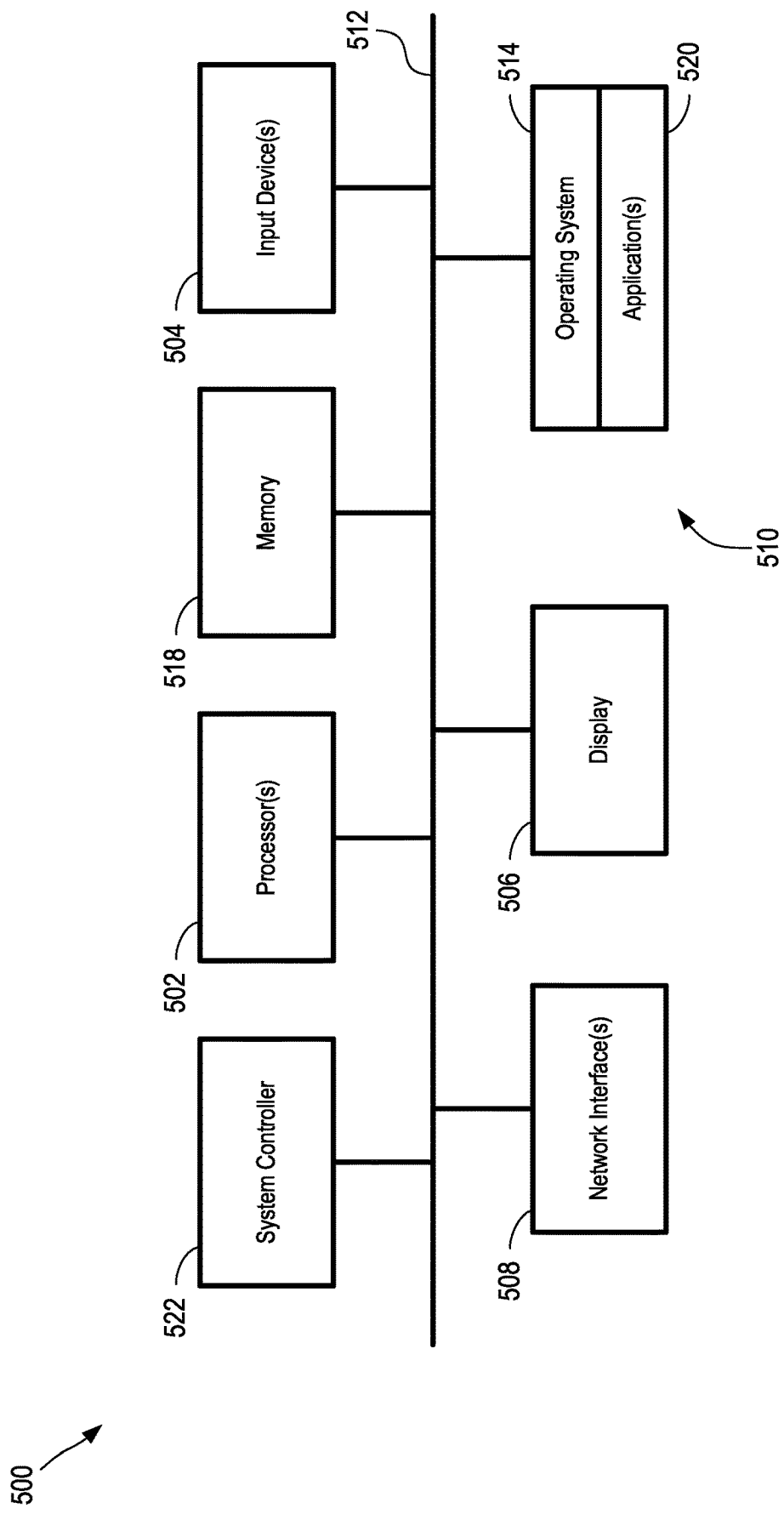
FIG. 5 is a block diagram depicting an example system architecture for implementing certain features and processes of the present disclosure

FIG. 5 is a block diagram of an example system architecture 500 for implementing features and processes of the present disclosure, such as those presented with reference to processes 200, 300, and 400 of FIGS. 2, 3, and 4, respectively. The architecture 500 can be used to implement a server (e.g., server 106 of FIG. 1), a user device (e.g., user device 102 of FIG. 1), or any other suitable device for performing some or all of the aspects of the present disclosure. The architecture 500 can be implemented on any electronic device that runs software applications derived from compiled instructions, including without limitation personal computers, servers, smart phones, electronic tablets, game consoles, email devices, and the like. In some implementations, the architecture 500 can include one or more processors 502, one or more input devices 504, one or more display devices 506, one or more network interfaces 508, and one or more computer-readable mediums 510. Each of these components can be coupled by bus 512.

Display device 506 can be any known display technology, including but not limited to display devices using Liquid Crystal Display (LCD) or Light Emitting Diode (LED) technology. Processor(s) 502 can use any known processor technology, including but not limited to graphics processors and multi-core processors. Input device 504 can be any known input device technology, including but not limited to a keyboard (including a virtual keyboard), mouse, track ball, and touch-sensitive pad or display. In some cases, audio inputs can be used to provide audio signals, such as audio signals of an individual speaking. Bus 512 can be any known internal or external bus technology, including but not limited to ISA, EISA, PCI, PCI Express, NuBus, USB, Serial ATA or FireWire.

Computer-readable medium 510 can be any medium that participates in providing instructions to processor(s) 502 for execution, including without limitation, non-volatile storage media (e.g., optical disks, magnetic disks, flash drives, etc.) or volatile media (e.g., SDRAM, ROM, etc.). The computer-readable medium (e.g., storage devices, mediums, and memories) can include, for example, a cable or wireless signal containing a bit stream and the like. However, when mentioned, non-transitory computer-readable storage media expressly exclude media such as energy, carrier signals, electromagnetic waves, and signals per se.

Computer-readable medium 510 can include various instructions for implementing operating system 514 and applications 520 such as computer programs. The operating system can be multi-user, multiprocessing, multitasking, multithreading, real-time and the like. The operating system 514 performs basic tasks, including but not limited to: recognizing input from input device 504; sending output to display device 506; keeping track of files and directories on computer-readable medium 510; controlling peripheral devices (e.g., storage drives, interface devices, etc.) which can be controlled directly or through an I/O controller; and managing traffic on bus 512. Computer-readable medium 510 can include various instructions for implementing firmware processes, such as a BIOS. Computer-readable medium 510 can include various instructions for implementing any of the processes described herein, including at least processes 200, 300, and 400 of FIGS. 2, 3, and 4, respectively.

Memory 518 can include high-speed random access memory and/or non-volatile memory, such as one or more magnetic disk storage devices, one or more optical storage devices, and/or flash memory (e.g., NAND, NOR). The memory 518 (e.g., computer-readable storage devices, mediums, and memories) can include a cable or wireless signal containing a bit stream and the like. However, when mentioned, non-transitory computer-readable storage media expressly exclude media such as energy, carrier signals, electromagnetic waves, and signals per se. The memory 518 can store an operating system, such as Darwin, RTXC, LINUX, UNIX, OS X, WINDOWS, or an embedded operating system such as VxWorks.

System controller 522 can be a service processor that operates independently of processor 502. In some implementations, system controller 522 can be a baseboard management controller (BMC). For example, a BMC is a specialized service processor that monitors the physical state of a computer, network server, or other hardware device using sensors and communicating with the system administrator through an independent connection. The BMC is configured on the motherboard or main circuit board of the device to be monitored. The sensors of a BMC can measure internal physical variables such as temperature, humidity, power-supply voltage, fan speeds, communications parameters and operating system (OS) functions.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., Objective-C, Java), including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computing system that includes a back-end component, such as a data server, or that includes a middleware component, such as an application server or an Internet server, or that includes a front-end component, such as a client computer having a graphical user interface or an Internet browser, or any combination thereof. The components of the system can be connected by any form or medium of digital data communication such as a communication network. Examples of communication networks include, e.g., a LAN, a WAN, and the computers and networks forming the Internet.

The computing system can include clients and servers. A client and server are generally remote from each other and typically interact through a network. The relationship of client and server arises by virtue of computer programs running on the respective computers and having a client-server relationship to each other.

One or more features or steps of the disclosed embodiments can be implemented using an application programming interface (API). An API can define one or more parameters that are passed between a calling application and other software code (e.g., an operating system, library routine, function) that provides a service, that provides data, or that performs an operation or a computation.

The API can be implemented as one or more calls in program code that send or receive one or more parameters through a parameter list or other structure based on a call convention defined in an API specification document. A parameter can be a constant, a key, a data structure, an object, an object class, a variable, a data type, a pointer, an array, a list, or another call. API calls and parameters can be implemented in any programming language. The programming language can define the vocabulary and calling convention that a programmer will employ to access functions supporting the API.

In some implementations, an API call can report to an application the capabilities of a device running the application, such as input capability, output capability, processing capability, power capability, communications capability, and the like.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art. Numerous changes to the disclosed embodiments can be made in accordance with the disclosure herein, without departing from the spirit or scope of the disclosure. Thus, the breadth and scope of the present disclosure should not be limited by any of the above described embodiments.

Although certain aspects and features of the present disclosure have been illustrated and described with respect to one or more implementations, equivalent alterations and modifications will occur or be known to others skilled in the art upon the reading and understanding of this specification and the annexed drawings. In addition, while a particular feature may have been disclosed with respect to only one of several implementations, such feature may be combined with one or more other features of the other implementations as may be desired and advantageous for any given or particular application.

The terminology used herein is for the purpose of describing particular embodiments only, and is not intended to be limiting of the disclosure. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

As used below, any reference to a series of examples is to be understood as a reference to each of those examples disjunctively (e.g., "Examples 1-4" is to be understood as "Examples 1, 2, 3, or 4").

Example 1 is a system, comprising: one or more data processors; and a non-transitory computer-readable storage medium containing instructions which, when executed on the one or more data processors, cause the one or more data processors to perform operations including: receiving a first evaluation associated with a goal at a first time; receiving a second evaluation associated with the goal at a second time; determining a trend using the first evaluation and the second evaluation, wherein the trend is associated with a period of time between the first time and the second time; presenting an explanation request in response to determining the trend; receiving an explanation response containing an explanation phrase; storing the explanation phrase in association with the trend; receiving a third evaluation associated with the goal at a third time; determining a subsequent trend using the third evaluation, wherein the subsequent trend is associated with a period of time including the third time; and presenting an empathic communication in response to determining the subsequent trend, wherein the empathic communication is associated with the goal, and wherein presenting the empathic communication includes: accessing a recipe database; selecting a recipe from the recipe database using the subsequent trend; and generating the empathic communication using the selected recipe and the explanation phrase, wherein the empathic communication includes the explanation phrase.

Example 2 is the system of example(s) 1, wherein the goal is a mood, wherein the first evaluation is indicative of a first mood of a user, wherein the second evaluation is indicative of a second mood of the user, and wherein the third evaluation is indicative of a third mood of the user.

Example 3 is the system of example(s) 1 or 2, wherein presenting the explanation request includes presenting an input field for free text, and wherein receiving the explanation response includes storing the free text as the explanation phrase.

Example 4 is the system of example(s) 1-3, selecting the recipe from the recipe database using the subsequent trend includes: comparing the subsequent trend with the trend; and selecting the selected recipe based on the comparison between the subsequent trend and the trend.

Example 5 is the system of example(s) 4, wherein comparing the subsequent trend with the trend includes identifying the subsequent trend as being consistent with or inconsistent with the trend, wherein selecting the selected recipe based on the comparison between the subsequent trend and the trend includes: selecting a first recipe when the subsequent trend is identified as being consistent with the trend; and selecting a second recipe when the subsequent trend is identified as being inconsistent with the trend.

Example 6 is the system of example(s) 5, wherein determining the trend includes identifying the trend as a positive trend when the second evaluation is indicative of a positive movement towards reaching the goal between the first time and the second time, wherein the second recipe includes a recommendation to employ the explanation phrase.

Example 7 is the system of example(s) 1-6, wherein the operations further comprise receiving a fourth evaluation associated with the goal at a fourth time, wherein determining the subsequent trend further includes using the fourth evaluation, wherein the subsequent trend is associated with a period of time between the third time and the fourth time.

Example 8 is the system of example(s) 1-7, wherein the operations further comprise: determining one or more additional subsequent trends after presenting the empathic communication; evaluating the selected recipe using the one or more additional subsequent trends; and presenting a subsequent empathic communication, wherein presenting the subsequent empathic communication includes: accessing the recipe database; selecting a subsequent recipe from the recipe database using the subsequent trend and the evaluation of the selected recipe, wherein the subsequent recipe is different from the recipe; and generating the subsequent empathic communication using the subsequent recipe.

Example 9 is the system of example(s) 1-8, wherein the operations further comprise preprocessing the explanation phrase prior to storing the explanation phrase, wherein preprocessing the explanation phrase includes processing the explanation phrase as a text string.

Example 10 is the system of example(s) 9, wherein preprocessing the explanation phrase includes applying a copout classifier to the explanation phrase, and wherein storing the explanation phrase occurs in response to classifying the explanation phrase as not a copout.

Example 11 is a computer-implemented method, comprising: receiving a first evaluation associated with a goal at a first time; receiving a second evaluation associated with the goal at a second time; determining a trend using the first evaluation and the second evaluation, wherein the trend is associated with a period of time between the first time and the second time; presenting an explanation request in response to determining the trend; receiving an explanation response containing an explanation phrase; storing the explanation phrase in association with the trend; receiving a third evaluation associated with the goal at a third time; determining a subsequent trend using the third evaluation, wherein the subsequent trend is associated with a period of time including the third time; and presenting an empathic communication in response to determining the subsequent trend, wherein the empathic communication is associated with the goal, and wherein presenting the empathic communication includes: accessing a recipe database; selecting a recipe from the recipe database using the subsequent trend; and generating the empathic communication using the selected recipe and the explanation phrase, wherein the empathic communication includes the explanation phrase.

Example 12 is the method of example(s) 11, wherein the goal is a mood, wherein the first evaluation is indicative of a first mood of a user, wherein the second evaluation is indicative of a second mood of the user, and wherein the third evaluation is indicative of a third mood of the user.

Example 13 is the method of example(s) 11 or 12, wherein presenting the explanation request includes presenting an input field for free text, and wherein receiving the explanation response includes storing the free text as the explanation phrase.

Example 14 is the method of example(s) 11-13, selecting the recipe from the recipe database using the subsequent trend includes: comparing the subsequent trend with the trend; and selecting the selected recipe based on the comparison between the subsequent trend and the trend.

Example 15 is the method of example(s) 14, wherein comparing the subsequent trend with the trend includes identifying the subsequent trend as being consistent with or inconsistent with the trend, wherein selecting the selected recipe based on the comparison between the subsequent trend and the trend includes: selecting a first recipe when the subsequent trend is identified as being consistent with the trend; and selecting a second recipe when the subsequent trend is identified as being inconsistent with the trend.

Example 16 is the method of example(s) 15, wherein determining the trend includes identifying the trend as a positive trend when the second evaluation is indicative of a positive movement towards reaching the goal between the first time and the second time, wherein the second recipe includes a recommendation to employ the explanation phrase.

Example 17 is the method of example(s) 11-16, further comprising receiving a fourth evaluation associated with the goal at a fourth time, wherein determining the subsequent trend further includes using the fourth evaluation, wherein the subsequent trend is associated with a period of time between the third time and the fourth time.

Example 18 is the method of example(s) 11-17, further comprising: determining one or more additional subsequent trends after presenting the empathic communication; evaluating the selected recipe using the one or more additional subsequent trends; and presenting a subsequent empathic communication, wherein presenting the subsequent empathic communication includes: accessing the recipe database; selecting a subsequent recipe from the recipe database using the subsequent trend and the evaluation of the selected recipe, wherein the subsequent recipe is different from the recipe; and generating the subsequent empathic communication using the subsequent recipe.

Example 19 is the method of example(s) 11-18, further comprising preprocessing the explanation phrase prior to storing the explanation phrase, wherein preprocessing the explanation phrase includes processing the explanation phrase as a text string.

Example 20 is the method of example(s) 19, wherein preprocessing the explanation phrase includes applying a copout classifier to the explanation phrase, and wherein storing the explanation phrase occurs in response to classifying the explanation phrase as not a copout.

Example 21 is a computer-program product tangibly embodied in a non-transitory machine-readable storage medium, including instructions configured to cause a data processing apparatus to perform operations including: receiving a first evaluation associated with a goal at a first time; receiving a second evaluation associated with the goal at a second time; determining a trend using the first evaluation and the second evaluation, wherein the trend is associated with a period of time between the first time and the second time; presenting an explanation request in response to determining the trend; receiving an explanation response containing an explanation phrase; storing the explanation phrase in association with the trend; receiving a third evaluation associated with the goal at a third time; determining a subsequent trend using the third evaluation, wherein the subsequent trend is associated with a period of time including the third time; and presenting an empathic communication in response to determining the subsequent trend, wherein the empathic communication is associated with the goal, and wherein presenting the empathic communication includes: accessing a recipe database; selecting a recipe from the recipe database using the subsequent trend; and generating the empathic communication using the selected recipe and the explanation phrase, wherein the empathic communication includes the explanation phrase.

Example 22 is the computer-program product of example(s) 21, wherein the goal is a mood, wherein the first evaluation is indicative of a first mood of a user, wherein the second evaluation is indicative of a second mood of the user, and wherein the third evaluation is indicative of a third mood of the user.

Example 23 is the computer-program product of example(s) 21 or 22, wherein presenting the explanation request includes presenting an input field for free text, and wherein receiving the explanation response includes storing the free text as the explanation phrase.

Example 24 is the computer-program product of example(s) 21,-23 selecting the recipe from the recipe database using the subsequent trend includes: comparing the subsequent trend with the trend; and selecting the selected recipe based on the comparison between the subsequent trend and the trend.

Example 25 is the computer-program product of example(s) 24, wherein comparing the subsequent trend with the trend includes identifying the subsequent trend as being consistent with or inconsistent with the trend, wherein selecting the selected recipe based on the comparison between the subsequent trend and the trend includes: selecting a first recipe when the subsequent trend is identified as being consistent with the trend; and selecting a second recipe when the subsequent trend is identified as being inconsistent with the trend.

Example 26 is the computer-program product of example(s) 25, wherein determining the trend includes identifying the trend as a positive trend when the second evaluation is indicative of a positive movement towards reaching the goal between the first time and the second time, wherein the second recipe includes a recommendation to employ the explanation phrase.

Example 27 is the computer-program product of example(s) 21-26, wherein the operations further comprise receiving a fourth evaluation associated with the goal at a fourth time, wherein determining the subsequent trend further includes using the fourth evaluation, wherein the subsequent trend is associated with a period of time between the third time and the fourth time.

Example 28 is the computer-program product of example(s) 21-27, wherein the operations further comprise: determining one or more additional subsequent trends after presenting the empathic communication; evaluating the selected recipe using the one or more additional subsequent trends; and presenting a subsequent empathic communication, wherein presenting the subsequent empathic communication includes: accessing the recipe database; selecting a subsequent recipe from the recipe database using the subsequent trend and the evaluation of the selected recipe, wherein the subsequent recipe is different from the recipe; and generating the subsequent empathic communication using the subsequent recipe.

Example 29 is the computer-program product of example(s) 21-28, wherein the operations further comprise preprocessing the explanation phrase prior to storing the explanation phrase, wherein preprocessing the explanation phrase includes processing the explanation phrase as a text string.

Example 30 is the computer-program product of example(s) 29, wherein preprocessing the explanation phrase includes applying a copout classifier to the explanation phrase, and wherein storing the explanation phrase occurs in response to classifying the explanation phrase as not a copout.

Example 31 is a method, comprising: receiving user input from a user at a first time, wherein the user input includes an input phrase; storing the input phrase, wherein the stored input phrase is associated with the user; receiving a trigger at a second time after the first time; and presenting an empathic communication to the user in response to receiving the trigger, wherein presenting the empathic communication includes: accessing the stored input phrase; and generating the empathic communication using the stored input phrase, wherein the generated empathic communication includes at least a portion of the input phrase.

Example 32 is the method of example(s) 31, wherein the user input is associated with a first topic, wherein receiving the trigger includes identifying a second topic, wherein the method further comprises comparing the second topic to the first topic to generate a comparison, and wherein presenting the empathic communication includes using the comparison between the second topic and the first topic.

Example 33 is the method of example(s) 32, wherein the first topic is a goal, and wherein the input phrase is an explanation phrase associated with the goal.

Example 34 is the method of example(s) 33, wherein receiving the trigger includes identifying a trend associated with the goal.

Example 35 is a system comprising: a control system including one or more processors; and a memory having stored thereon machine readable instructions; wherein the control system is coupled to the memory, and the method of any one of example(s) 31-34 is implemented when the machine executable instructions in the memory are executed by at least one of the one or more processors of the control system.

Example 36 is a system for communicating with empathy, the system including a control system configured to implement the method of any one of example(s) 31-34.

Example 37 is a computer program product comprising instructions which, when executed by a computer, cause the computer to carry out the method of any one of example(s) 31 to 34.

Example 38 is the computer program product of example(s) 37, wherein the computer program product is a non-transitory computer readable medium.

What is claimed is:

1. A system, comprising:
one or more data processors; and
a non-transitory computer-readable storage medium containing instructions which, when executed on the one or more data processors, cause the one or more data processors to perform operations including:
receiving a first evaluation associated with a goal at a first time;
receiving a second evaluation associated with the goal at a second time;
determining a trend using the first evaluation and the second evaluation, wherein the trend is associated with a period of time between the first time and the second time;
presenting an explanation request in response to determining the trend;
receiving an explanation response containing an explanation phrase;
storing, in an explanation database, the explanation phrase in association with the trend;
receiving a third evaluation associated with the goal at a third time;
determining a subsequent trend using the third evaluation, wherein the subsequent trend is associated with a period of time including the third time;
presenting an empathic communication in response to determining the subsequent trend, wherein the empathic communication is associated with the goal, and wherein presenting the empathic communication includes:
accessing a recipe database;
selecting a recipe from the recipe database using the subsequent trend;
accessing the stored explanation phrase from the explanation database; and
generating the empathic communication using the selected recipe and the stored explanation phrase, wherein the empathic communication includes the stored explanation phrase;
determining one or more additional subsequent trends after presenting the empathic communication;
evaluating the selected recipe using the one or more additional subsequent trends; and
presenting a subsequent empathic communication, wherein presenting the subsequent empathic communication includes:
accessing the recipe database;
selecting a subsequent recipe from the recipe database using the subsequent trend and the evaluation of the selected recipe wherein the subsequent recipe is different from the recipe; and
generating the subsequent empathic communication using the subsequent recipe and the stored explanation phrase.

2. The system of claim 1, wherein the goal is a mood, wherein the first evaluation is indicative of a first mood of a user, wherein the second evaluation is indicative of a second mood of the user, and wherein the third evaluation is indicative of a third mood of the user.

3. The system of claim 1, wherein presenting the explanation request includes presenting an input field for free text, and wherein receiving the explanation response includes storing the free text as the explanation phrase.

4. The system of claim 1, wherein selecting the recipe from the recipe database using the subsequent trend includes:
comparing the subsequent trend with the trend; and
selecting the selected recipe based on the comparison between the subsequent trend and the trend.

5. The system of claim 4, wherein comparing the subsequent trend with the trend includes identifying the subsequent trend as being consistent with or inconsistent with the trend, wherein selecting the selected recipe based on the comparison between the subsequent trend and the trend includes:
selecting a first recipe when the subsequent trend is identified as being consistent with the trend; and
selecting a second recipe when the subsequent trend is identified as being inconsistent with the trend.

6. The system of claim 5, wherein determining the trend includes identifying the trend as a positive trend when the second evaluation is indicative of a positive movement towards reaching the goal between the first time and the second time, wherein the second recipe includes a recommendation to employ the explanation phrase.

7. The system of claim 1, wherein the operations further comprise receiving a fourth evaluation associated with the goal at a fourth time, wherein determining the subsequent trend further includes using the fourth evaluation, wherein the subsequent trend is associated with a period of time between the third time and the fourth time.

8. The system of claim 1, wherein the operations further comprise preprocessing the explanation phrase prior to storing the explanation phrase, wherein preprocessing the explanation phrase includes processing the explanation phrase as a text string.

9. The system of claim 8, wherein preprocessing the explanation phrase includes applying a copout classifier to the explanation phrase, and wherein storing the explanation phrase occurs in response to classifying the explanation phrase as not a copout.

10. A computer-implemented method, comprising:
- receiving a first evaluation associated with a goal at a first time;
- receiving a second evaluation associated with the goal at a second time;
- determining a trend using the first evaluation and the second evaluation, wherein the trend is associated with a period of time between the first time and the second time;
- presenting an explanation request in response to determining the trend;
- receiving an explanation response containing an explanation phrase;
- storing, in an explanation database, the explanation phrase in association with the trend;
- receiving a third evaluation associated with the goal at a third time;
- determining a subsequent trend using the third evaluation, wherein the subsequent trend is associated with a period of time including the third time;
- presenting an empathic communication in response to determining the subsequent trend, wherein the empathic communication is associated with the goal, and wherein presenting the empathic communication includes:
  - accessing a recipe database;
  - selecting a recipe from the recipe database using the subsequent trend;
  - accessing the stored explanation phrase from the explanation database; and
  - generating the empathic communication using the selected recipe and the stored explanation phrase, wherein the empathic communication includes the stored explanation phrase;
- determining one or more additional subsequent trends after presenting the empathic communication;
- evaluating the selected recipe using the one or more additional subsequent trends; and
- presenting a subsequent empathic communication, wherein presenting the subsequent empathic communication includes:
  - accessing the recipe database;
  - selecting a subsequent recipe from the recipe database using the subsequent trend and the evaluation of the selected recipe, wherein the subsequent recipe is different from the recipe; and
  - generating the subsequent empathic communication using the subsequent recipe and the stored explanation phrase.

11. The method of claim 10, wherein the goal is a mood, wherein the first evaluation is indicative of a first mood of a user, wherein the second evaluation is indicative of a second mood of the user, and wherein the third evaluation is indicative of a third mood of the user.

12. The method of claim 10, wherein presenting the explanation request includes presenting an input field for free text, and wherein receiving the explanation response includes storing the free text as the explanation phrase.

13. The method of claim 10, wherein selecting the recipe from the recipe database using the subsequent trend includes:
- comparing the subsequent trend with the trend; and
- selecting the selected recipe based on the comparison between the subsequent trend and the trend.

14. The method of claim 13, wherein comparing the subsequent trend with the trend includes identifying the subsequent trend as being consistent with or inconsistent with the trend, wherein selecting the selected recipe based on the comparison between the subsequent trend and the trend includes:
- selecting a first recipe when the subsequent trend is identified as being consistent with the trend; and
- selecting a second recipe when the subsequent trend is identified as being inconsistent with the trend.

15. The method of claim 14, wherein determining the trend includes identifying the trend as a positive trend when the second evaluation is indicative of a positive movement towards reaching the goal between the first time and the second time, wherein the second recipe includes a recommendation to employ the explanation phrase.

16. The method of claim 10, further comprising receiving a fourth evaluation associated with the goal at a fourth time, wherein determining the subsequent trend further includes using the fourth evaluation, wherein the subsequent trend is associated with a period of time between the third time and the fourth time.

17. The method of claim 10, further comprising preprocessing the explanation phrase prior to storing the explanation phrase, wherein preprocessing the explanation phrase includes processing the explanation phrase as a text string.

18. The method of claim 17, wherein preprocessing the explanation phrase includes applying a copout classifier to the explanation phrase, and wherein storing the explanation phrase occurs in response to classifying the explanation phrase as not a copout.

19. A computer-program product tangibly embodied in a non-transitory machine-readable storage medium, including instructions configured to cause a data processing apparatus to perform operations including:
- receiving a first evaluation associated with a goal at a first time;
- receiving a second evaluation associated with the goal at a second time;
- determining a trend using the first evaluation and the second evaluation, wherein the trend is associated with a period of time between the first time and the second time;
- presenting an explanation request in response to determining the trend;
- receiving an explanation response containing an explanation phrase;
- storing, in an explanation database, the explanation phrase in association with the trend;
- receiving a third evaluation associated with the goal at a third time;
- determining a subsequent trend using the third evaluation, wherein the subsequent trend is associated with a period of time including the third time;

presenting an empathic communication in response to determining the subsequent trend, wherein the empathic communication is associated with the goal, and wherein presenting the empathic communication includes:
  accessing a recipe database;
  selecting a recipe from the recipe database using the subsequent trend;
  accessing the stored explanation phrase from the explanation database; and
  generating the empathic communication using the selected recipe and the stored explanation phrase, wherein the empathic communication includes the stored explanation phrase;
determining one or more additional subsequent trends after presenting the empathic communication;
evaluating the selected recipe using the one or more additional subsequent trends; and
presenting a subsequent empathic communication, wherein presenting the subsequent empathic communication includes:
  accessing the recipe database;
  selecting a subsequent recipe from the recipe database using the subsequent trend and the evaluation of the selected recipe, wherein the subsequent recipe is different from the recipe; and
  generating the subsequent empathic communication using the subsequent recipe and the stored explanation phrase.

20. The computer-program product of claim 19, wherein the goal is a mood, wherein the first evaluation is indicative of a first mood of a user, wherein the second evaluation is indicative of a second mood of the user, and wherein the third evaluation is indicative of a third mood of the user.

21. The computer-program product of claim 19, wherein presenting the explanation request includes presenting an input field for free text, and wherein receiving the explanation response includes storing the free text as the explanation phrase.

22. The computer-program product of claim 19, wherein selecting the recipe from the recipe database using the subsequent trend includes:
  comparing the subsequent trend with the trend; and
  selecting the selected recipe based on the comparison between the subsequent trend and the trend.

23. The computer-program product of claim 22, wherein comparing the subsequent trend with the trend includes identifying the subsequent trend as being consistent with or inconsistent with the trend, wherein selecting the selected recipe based on the comparison between the subsequent trend and the trend includes:
  selecting a first recipe when the subsequent trend is identified as being consistent with the trend; and
  selecting a second recipe when the subsequent trend is identified as being inconsistent with the trend.

24. The computer-program product of claim 23, wherein determining the trend includes identifying the trend as a positive trend when the second evaluation is indicative of a positive movement towards reaching the goal between the first time and the second time, wherein the second recipe includes a recommendation to employ the explanation phrase.

25. The computer-program product of claim 19, wherein the operations further comprise receiving a fourth evaluation associated with the goal at a fourth time, wherein determining the subsequent trend further includes using the fourth evaluation, wherein the subsequent trend is associated with a period of time between the third time and the fourth time.

26. The computer-program product of claim 19 wherein the operations further comprise preprocessing the explanation phrase prior to storing the explanation phrase, wherein preprocessing the explanation phrase includes processing the explanation phrase as a text string.

27. The computer-program product of claim 26, wherein preprocessing the explanation phrase includes applying a copout classifier to the explanation phrase, and wherein storing the explanation phrase occurs in response to classifying the explanation phrase as not a copout.

* * * * *